US00PP10322P

United States Patent [19]

Kientzler

[11] Patent Number: Plant 10,322

[45] Date of Patent: Apr. 7, 1998

[54] NEW GUINEA IMPATIENS PLANT NAMED 'LYCIA'

[75] Inventor: Ludwig Kientzler, Gensingen, Germany

[73] Assignee: Paul Ecke Ranch, Inc., Encinitas, Calif.

[21] Appl. No.: 778,880

[22] Filed: Jan. 3, 1997

[51] Int. Cl.[6] ..... A01H 5/00

[52] U.S. Cl. ..... Plt./87.6

[58] Field of Search ..... Plt./87.6

*Primary Examiner*—James R. Feyrer
*Attorney, Agent, or Firm*—C. A. Whealy

[57] ABSTRACT

A new and distinct cultivar of New Guinea Impatiens plant named 'Lycia', characterized by its flat and rounded to star-shaped orange and light pink bi-colored flowers; outwardly spreading and mounded growth habit; and dark green, somewhat glossy, non-variegated foliage.

1 Drawing Sheet

The present invention relates to a new and distinct cultivar of New Guinea Impatiens plant, botanically known as *Impatiens hawkeri*, known by the name 'Kilyc', and hereinafter referred to by the cultivar name 'Lycia', The new cultivar is a product of a planned breeding program conducted by the inventor in Gensingen, Germany. The objective of the breeding program was to develop new varieties that have a uniform plant habit, attractive flower colors, good flower form and numerous flowers per plant.

The new cultivar originated from a cross made by the inventor of a proprietary seedling selection identified as P905 as the male, or pollen parent, with the proprietary seedling selection identified as L34 as the female, or seed patent. The cultivar 'Lycia ' was discovered and selected by the inventor as a flowering plant within the progeny of the stated cross in a controlled environment in Gensingen, Germany. Asexual reproduction of the new cultivar by terminal cuttings taken at Gensingen, Germany, has shown that the unique features of this new Impatiens are stable and reproduced true to type in successive generations of asexual reproduction.

The following traits have been repeatedly observed and are determined to be the unique characteristics of 'Lycia'. These characteristics in combination distinguish 'Lycia' as a new and distinct cultivar:

1. Flat and rounded to star-shaped orange and light pink bi-colored flowers.
2. Outwardly spreading and mounded growth habit.
3. Dark green, somewhat glossy, non-variegated foliage.

The accompanying colored photographs illustrate the overall appearance of the new cultivar, showing the colors as true as it is reasonably possible to obtain in colored reproductions of this type.

The first photograph comprises a top perspective view of a typical plant of 'Lycia'.

The second photograph comprises a close-up view of a typical flower and upper (left) and lower (right) surfaces of leaves of the variety 'Lycia'.

Flower and foliage colors in the photographs may differ from the actual colors due to light reflectance.

The cultivar 'Lycia' has not been observed under all possible environmental conditions. The phenotype may vary somewhat with variations in environment such as temperature and light intensity, without, however, any variance in genotype. The following observations, measurements and comparisons describe plants grown 10-cm pots in Encinitas, Calif., under commercial practice in a fiberglass-covered greenhouse with day temperatures ranging from 23 to 29C. and night temperatures ranging from 16 to 18C. and light levels averaging 3,000 footcandles.

In the following description, color references are made to The Royal Horticultural Society Colour Chart except where general terms of ordinary dictionary significance are used.

Classification:

*Botanical.*—*Impatiens hawkeri* 'Lycia'.

*Commercial.*—New Guinea Impatiens cv. 'Lycia'.

Parentage:

*Male parent.*—Proprietary seeding selection P905.

*Female parent.*—Proprietary seedling selection L32.

Propagation:

*Type cutting.*—Terminal cuttings.

*Time to initiate roots.*—About 15 days with 21C. soil temperature.

Plant description:

*Plant form.*—Outwardly spreading and mounded.

*Growth habit.*—Moderately vigorous and moderate branching. Suitable for 10 to 25-cm containers.

*Plant size.*—Height: About 16 cm. Width or spread: About 32 cm.

*Lateral branches.*—Quantity: Five to six. Size: Length: About 14 cm. Diameter: About 1.2 cm. Internode length: About 5.5 cm. Color: 144A with 59A streaks.

*Foliage description.*—Leaves simple, generally symmetrical, abundant, opposite or in whorls of three, horizontal to plant and flat in aspect. Size, largest leaves: Length: About 11 cm. Width: About 5 cm. Shape: Ovate with acuminate apex, attenuate base and ciliate margin. Texture: Smooth, somewhat glossy. Color: Young foliage, upper surface: 146A with 59A overtones. Young foliage, lower surface: 59A. Fully expanded foliage, upper surface: 147A. Fully expanded foliage, lower surface: 59A. Venation, upper surface: 59A. Venation, lower surface: 59A. Petiole: Size: Length: About 3.25 cm. Diameter: About 3 mm. Color: 59A.

Flower description:

*Flower type and habit.*—Orange and light pink bi-colored flowers. Moderate to freely and continuously flowering. Flowers arise from leaf axils. Usually seven to eight flowers per lateral branch. Flowers positioned at or slightly below the foliage and face upward or outward. Flowers flat and rounded to star-shaped. Flowers persistent.

*Flowering season.*—Year-round under greenhouse conditions. In the garden, flowering is continuous from spring until fall.

*Flower size.*—Length: About 7.5 cm. Width: About 6.5 cm. Depth: About 3 mm.

*Flower buds.*—Size: Length: About 1.7 cm. Diameter: About 1.1 cm. Shape: Ovoid. Color: 40A.

*Petals.*—Quantity: Five. Size (largest petals): Length: Top petal: About 3.5 cm. Middle petals: About 3.5 cm. Bottom petals: About 3.5 cm. Width: Top petal: About 5 cm. Middle petals: About 3.5 cm. Bottom petals: About 4 cm. Shape: Cordate with emarginate apex, cuneate or obtuse base and entire margin. Texture: Smooth. Color: When opening, upper surface: Iridescent, 50D background with 33A centers and midribs, 57A at base. When opening, lower surface: Iridescent, 40B with 57A at base. Fully opened, upper surface: Iridescent, 50D background with 33A centers and midribs, 57A at base. Fully opened, lower surface: Iridescent, 40B with 57A at base. Fading to: Petal color does not fade.

*Spur.*—Length: About 4.5 cm. Shape: Narrow and curved. Color: Proximal: 59B. Distal: 144A.

*Peduncles.*—Length: About 2.5 cm. Angle: Mostly outward. Strength: Strong. Color: 144A.

*Reproductive organs.*—Androecium: Stamen number: Five, anthers fused, filaments free. Anther shape: Obovate. Anther size: 6 by 4 mm. Anther color: Light yellow. Amount of pollen: Moderate. Pollen color: Cream. Gynoecium: Five-loculate fused. Stigma color: White. Gynoecium color: 144A to darker than 59A.

Disease resistance: Under commercial conditions, resistance nor susceptibility to pathogens has not been observed.

Seed development: Seed production is not usually observed.

It is claimed:

1. A new and distinct cultivar of New Guinea Impatiens plant named 'Lycia', illustrated and described.

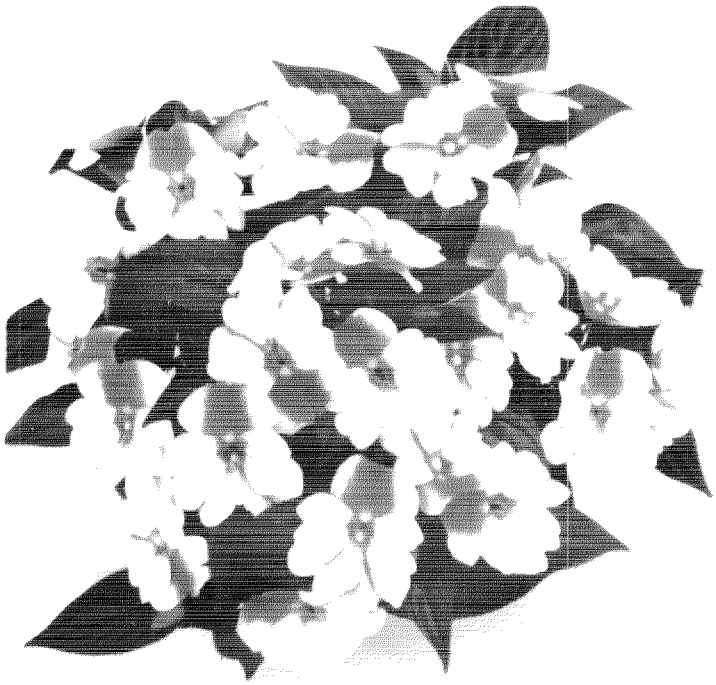
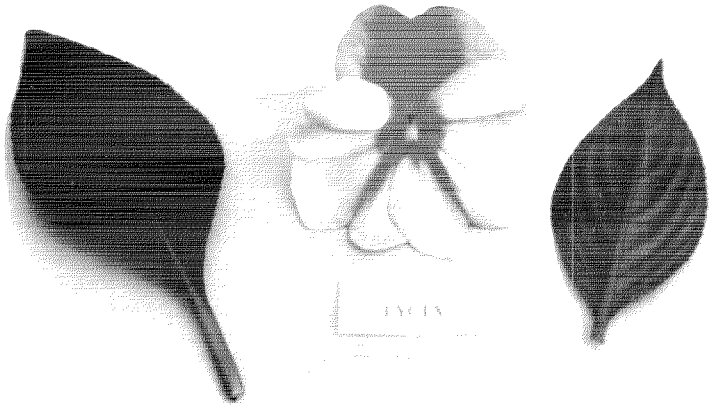

* * * * *